United States Patent
Minai et al.

(10) Patent No.: US 9,443,321 B2
(45) Date of Patent: Sep. 13, 2016

(54) IMAGING DEVICE, ENDOSCOPE SYSTEM AND IMAGING METHOD USING YELLOW-ELIMINATED GREEN DATA

(75) Inventors: Tetsuo Minai, Hachioji (JP); Kazuaki Tamura, Hachioji (JP); Takeshi Mori, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 1528 days.

(21) Appl. No.: 12/760,720

(22) Filed: Apr. 15, 2010

(65) Prior Publication Data

US 2010/0265322 A1    Oct. 21, 2010

Related U.S. Application Data

(63) Continuation of application No. PCT/JP2009/067863, filed on Oct. 15, 2009.

(30) Foreign Application Priority Data

Oct. 17, 2008    (JP) ................. 2008-268896

(51) Int. Cl.
*A61B 1/04*    (2006.01)
*G06T 7/40*    (2006.01)
(Continued)

(52) U.S. Cl.
CPC ........... *G06T 7/408* (2013.01); *A61B 1/00009* (2013.01); *A61B 1/041* (2013.01);
(Continued)

(58) Field of Classification Search
USPC .................. 348/61, 71, 77; 345/88
IPC ...................................................... A61B 1/04
See application file for complete search history.

(56) References Cited

U.S. PATENT DOCUMENTS

2003/0001104 A1    1/2003  Sendai et al.
2009/0023991 A1    1/2009  Gono et al.
(Continued)

FOREIGN PATENT DOCUMENTS

CN        101637379 A      2/2010
EP    JP 2007-244681 A     9/2007
(Continued)

OTHER PUBLICATIONS

Song, W.K., et al, Prepared by ASGE Technology Committee, "Narrow Band Imaging and Multiband Imaging", Gastrointestinal Endoscopy, vol. 67, No. 4, Mar. 25, 2008, pp. 581-589.

(Continued)

*Primary Examiner* — Young Lee
(74) *Attorney, Agent, or Firm* — Scully, Scott, Murphy & Presser, PC (57) ABSTRACT

An image generating device includes a first image-information generating unit that generates first image information based on a plurality of pieces of acquired color element information, a color-component detecting unit that detects a predetermined color component based on each piece of color element information, a color-component eliminating unit that eliminates the predetermined color component detected by the color-component detecting unit from a predetermined piece of color element information among the plurality of pieces of color element information, and a second image-information generating unit that generates second color information based on a piece of color element information obtained by eliminating the predetermined color component by the color-component eliminating unit and another piece of color element information.

9 Claims, 5 Drawing Sheets

(51) Int. Cl.
    *A61B 1/06*     (2006.01)
    *A61B 1/00*     (2006.01)
    *G06T 7/00*     (2006.01)
    *G06T 11/00*     (2006.01)
    *A61B 5/00*     (2006.01)

(52) U.S. Cl.
    CPC .......... *A61B 1/0638* (2013.01); *A61B 1/0646* (2013.01); *G06T 7/00* (2013.01); *G06T 11/001* (2013.01); *A61B 5/0075* (2013.01); *A61B 5/0084* (2013.01); *G06T 2207/10068* (2013.01); *G06T 2207/30028* (2013.01); *G06T 2207/30092* (2013.01)

(56) References Cited

U.S. PATENT DOCUMENTS

2009/0040298 A1     2/2009     Yamazaki et al.
2009/0121992 A1*     5/2009     Asao et al. .................... 345/88
2010/0030021 A1     2/2010     Minai et al.

FOREIGN PATENT DOCUMENTS

| EP | 2 149 331 A1 | 2/2010 |
| JP | 4-197331 | 7/1992 |
| JP | 5-332838 | 12/1993 |
| JP | 6-245899 | 9/1994 |
| JP | 2001-212073 | 8/2001 |
| JP | 2003-79568 | 3/2003 |
| JP | 2006-33639 | 2/2006 |
| JP | 2006-297093 | 11/2006 |
| JP | 2006-341078 | 12/2006 |
| JP | 2007-195023 | 8/2007 |

OTHER PUBLICATIONS

European Search Report dated Mar. 1, 2012 from corresponding European Patent Application No. EP 09 82 0624.6.

* cited by examiner

IMAGING DEVICE, ENDOSCOPE SYSTEM AND IMAGING METHOD USING YELLOW-ELIMINATED GREEN DATA

CROSS-REFERENCE TO RELATED APPLICATIONS

This application is a continuation of PCT international application Ser. No. PCT/JP2009/067863 filed on Oct. 15, 2009 which designates the United States, incorporated herein by reference.

BACKGROUND OF THE INVENTION

1. Field of the Invention

The present invention relates to an image generating device, an endoscope system, and an image generating method capable of simultaneously obtaining a normal image, which is a color image of an object illuminated with white light, and a spectral image, which is an image generated using a specific color component. The positional relation of the normal image and the spectral image is such that the images are of an identical object.

2. Description of the Related Art

In recent years, a capsule-shaped body-insertable apparatus (e.g., a capsule endoscope) equipped with an imaging function and a wireless communication function has been proposed, and a body-insertable apparatus system for capturing images of the inside of a subject by using the capsule endoscope has been developed. In order to enable observation (examination) of the inside of a subject, the capsule endoscope functions, from when it is swallowed from a mouth of the subject to when it is naturally excreted from the subject, such that it moves inside a body cavity, e.g., inside organs such as a stomach and a small intestine, by peristalsis and the like and captures images of the inside of the subject at, e.g., 0.5-second intervals.

While the capsule endoscope travels inside the subject, an external image display device receives images captured by the capsule endoscope via an antenna arranged on the body surface of the subject. The image display device has a wireless communication function for the capsule endoscope and a memory function for the images, and sequentially stores the images received from the capsule endoscope inside the subject in a memory. Doctors and nurses display the images accumulated in the image display device, i.e., the images of the inside of the digestive tract of the subject, on a display, so that they can observe (examine) the inside of the subject to make a diagnosis.

Japanese Laid-open Patent Publication No. 2006-297093 discloses a technology for applying a color filter array (CFA) in which the percentage of blue sensing elements is increased compared to those of red sensing elements and green sensing elements in order to obtain sharp images when in-vivo images are acquired. This technology is based on the fact that blue light has a shorter wavelength than other light and is reflected by the surface of a body tissue without reaching the inside of the body tissue to be scattered.

SUMMARY OF THE INVENTION

An image generating device according to an aspect of the invention includes: a first image-information generating unit that generates first image information based on a plurality of pieces of acquired color element information; a color-component detecting unit that detects a predetermined color component based on each piece of color element information; a color-component eliminating unit that eliminates the predetermined color component detected by the color-component detecting unit from a predetermined piece of color element information among the plurality of pieces of color element information; and a second image-information generating unit that generates second color information based on a piece of color element information obtained by eliminating the predetermined color component by the color-component eliminating unit and another piece of color element information, wherein the plurality of pieces of color element information are red data, green data, and blue data, the color-component detecting unit detects a yellow color component, the color-component eliminating unit generates yellow-eliminated green data by eliminating the yellow component from the green data, and the second image-information generating unit generates the second image information based on the yellow-eliminated green data and the blue data.

An endoscope system according to another aspect of the invention includes: a first image-information generating unit that generates first image information based on a plurality of pieces of acquired color element information; a color-component detecting unit that detects a predetermined color component based on each piece of color element information; a color-component eliminating unit that eliminates the predetermined color component detected by the color-component detecting unit from a predetermined piece of color element information among the plurality of pieces of color element information; and a second image-information generating unit that generates second color information based on a piece of color element information obtained by eliminating the predetermined color component by the color-component eliminating unit and another piece of color element information, wherein the plurality of pieces of color element information are red data, green data, and blue data, the color-component detecting unit detects a yellow color component, the color-component eliminating unit generates yellow-eliminated green data by eliminating the yellow component from the green data, and the second image-information generating unit generates the second image information based on the yellow-eliminated green data and the blue data.

An image generating method according to still another aspect of the invention includes: generating first image information based on acquired red data, green data, and blue data; calculating hue of the first image information; detecting a yellow component based on the hue calculated at the calculating; eliminating the yellow component from the green data; and generating second image information based on yellow-eliminated green data obtained by eliminating the yellow component from the green data at the eliminating and the blue data, wherein the plurality of color element information are red data, green data, and blue data, the yellow component is detected at the detecting, the yellow-eliminated green data is generated at the eliminating by eliminating the yellow color component from the green data, and the second image information is generated at the generating the second image information based on the yellow-eliminated green data and the blue data.

An image generating device according to still another aspect of the invention includes: a first image-information generating means that generates first image information based on a plurality of pieces of acquired color element information; a color-component detecting means that detects a predetermined color component based on each piece of color element information; a color-component eliminating means that eliminates the predetermined color component detected by the color-component detecting means from a predetermined piece of color element information among the plurality of pieces of color element information; and a second image-information generating means that generates second color information based on a piece of color element information obtained by eliminating the predetermined color component by the color-component eliminating means and another piece of color element information, wherein the plurality of pieces of color element information are red data, green data, and blue data, the color-component detecting means detects a yellow color component, the color-component eliminating means generates yellow-eliminated green data by eliminating the yellow component from the green data, and the second image-information generating means generates the second image information based on the yellow-eliminated green data and the blue data.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of an image generating device, an endoscope system that uses the image generating device, and an image generating method according to the present invention will be explained in detail below with reference to the accompanying drawings. In the following embodiments, a capsule endoscope is described as an example of an endoscope device in an endoscope system. However, the present invention is not limited by the embodiments.

Figure 1:
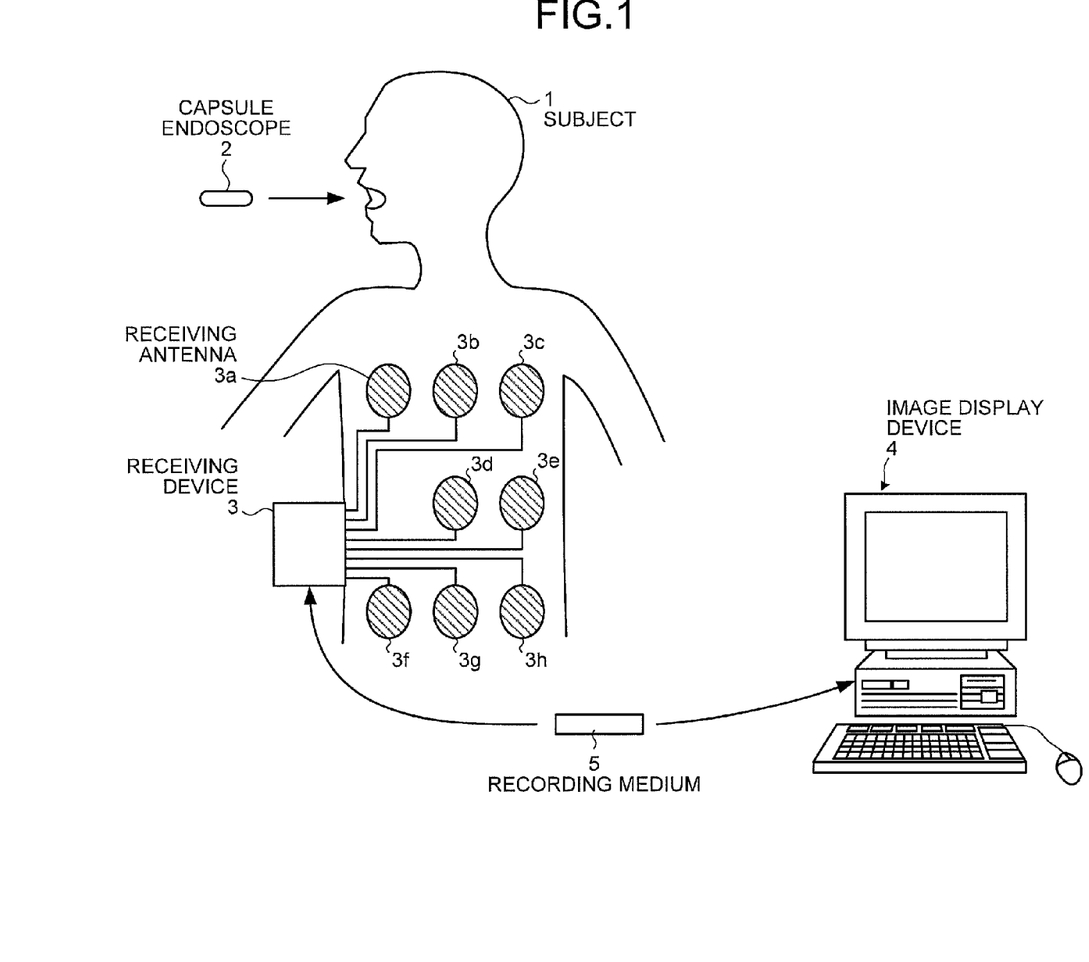
FIG. 1 is a diagram illustrating an entire general configuration of a capsule endoscope system as an endoscope system according to an embodiment of the present invention.

FIG. 1 is a schematic diagram illustrating a configuration of an endoscope system according to an embodiment of the present invention. As illustrated in FIG. 1, the endoscope system according to the embodiment includes a capsule endoscope 2 that captures in-vivo images of a subject 1, a receiving device 3 that receives image signals wirelessly transmitted by the capsule endoscope 2, an image display device 4 that displays the in-vivo images captured by the capsule endoscope 2, and a portable recording medium 5 for transfer and receipt of data between the receiving device 3 and the image display device 4.

Figure 2:
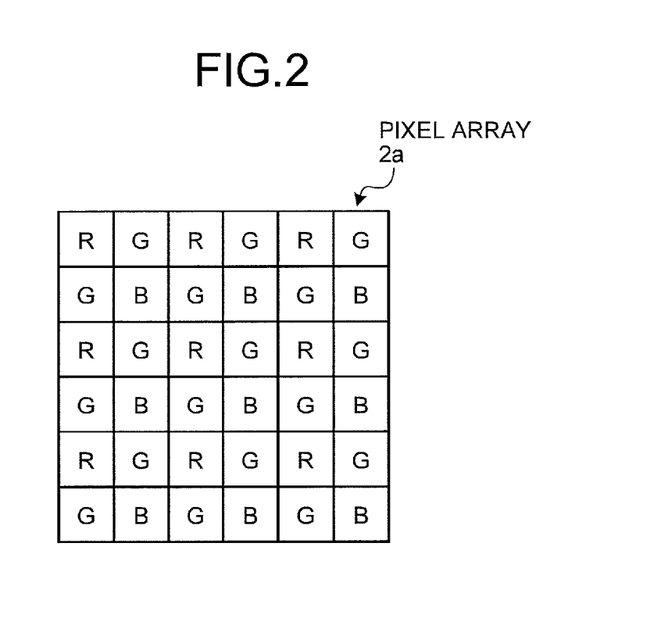
FIG. 2 is a diagram illustrating an example of a pixel array of an imaging device mounted in the capsule endoscope according to the embodiment of the present invention.

The capsule endoscope 2 is one example of an endoscope device that captures in-vivo images of the subject 1, and has an imaging function and a wireless communication function in a capsule-shaped casing. The capsule endoscope 2 is introduced into organs of the subject 1 via the oral route or the like, and sequentially captures in-vivo images of the subject 1 at predetermined intervals (e.g., at 0.5-second intervals) while travelling inside the organs of the subject 1 by peristalsis and the like. More specifically, the capsule endoscope 2 applies illumination light such as white light to an object inside the organs, and captures images of the object illuminated with the illumination light, i.e., in-vivo images of the subject 1. The capsule endoscope 2 wirelessly transmits image signals of the in-vivo images of the subject 1 thus captured to the receiving device 3 located outside. The capsule endoscope 2 repeats in-vivo image capturing operation and wireless transmission operation in sequence from when it is introduced into the organs of the subject 1 to when it is excreted out of the subject 1. As an imaging unit of the capsule endoscope 2, an imaging device in which red (R), green (G), and blue (B) pixels are arrayed as illustrated in FIG. 2 is used. In the embodiment, the imaging device with a Bayer array as illustrated in a pixel array 2a of FIG. 2 is used, in which G data has twice as much photosensitivity as that of R data or B data. Such an array is an array of a normal imaging device. Thus, a normal image (white light image) of the RGB data can be obtained. As a light emitting unit of the capsule endoscope, an LED that emits white light is used.

The receiving device 3 includes a plurality of receiving antennas 3a to 3h that are arranged to be dispersed at positions on the body surface of the subject 1, and receives wireless signals from the capsule endoscope 2 inside the subject 1 via at least one of the plurality of receiving antennas 3a to 3h. The receiving device 3 extracts image signals from among the wireless signals received from the capsule endoscope 2, and acquires image data of in-vivo images contained in the extracted image signals.

The receiving device 3 has an image generating function of generating two types of images using different image processing. The positional relation of the images is such that the images are of an identical object. The receiving device 3 performs the different image processing on color data of a one-frame in-vivo image acquired from the capsule endoscope 2, and generates the two types of images, e.g., a normal image, such as a white light image, and a spectral image. The positional relation of the images is such that the images are of an identical object and types of applied image processing are different. The normal image and the spectral image generated by the receiving device 3 are in-vivo images in each of which an identical object appears in a different drawing mode. Every time the receiving device 3 receives a one-frame in-vivo image from the capsule endoscope 2, the receiving device 3 sequentially generates the normal image and the spectral image of an identical object based on the acquired one-frame in-vivo image. The receiving device 3 accumulates a normal-image group and a spectral-image group in the recording medium 5 pre-attached thereto. In this case, the receiving device 3 sequentially stores the normal image and the spectral image of an identical object, which are generated from an identical in-vivo image, in the recording medium 5 as in-vivo images assigned with an identical frame number and subjected to different types of image processing. The receiving device 3 associates time data, such as imaging time or receiving time, of an original in-vivo image with each image in the white-light-image group and the spectral-image group.

The receiving antennas 3a to 3h of the receiving device 3 may be arranged on the body surface of the subject 1 as illustrated in FIG. 1, or may be arranged on a jacket that the subject 1 is to wear. The number of the receiving antennas of the receiving device 3 needs to be at least one, and is not limited to eight.

The image display device 4 has a configuration like a workstation that load various types of data such as an in-vivo image group of the subject 1 via the recording medium 5 and display the loaded various types of data of the in-vivo image group and the like. More specifically, the recording medium 5 detached from the receiving device 3 is attached to the image display device 4, and the image display device 4 loads data stored in the recording medium 5 to thereby acquire the various types of data of the in-vivo image group (the normal-image group and the spectral-image group) of the subject 1. The image display device 4 has a display switching function of displaying the acquired in-vivo images on a display, and switching between identical-object images that contain a desired image area specified in the displayed in-vivo images and that are subjected to different types of image processing. With the image display by the image display device 4, diagnosis and the like is performed.

The recording medium 5 is a portable recording medium for transfer and receipt of data between the receiving device 3 and the image display device 4 described above. The recording medium 5 is configured to be detachably attached to the receiving device 3 and the image display device 4, and be able to output and record data when attached to the receiving device 3 and the image display device 4. More specifically, when attached to the receiving device 3, the recording medium 5 records therein the in-vivo image group subjected to image processing by the receiving device 3, time data of each image, and the like.

Figure 3:
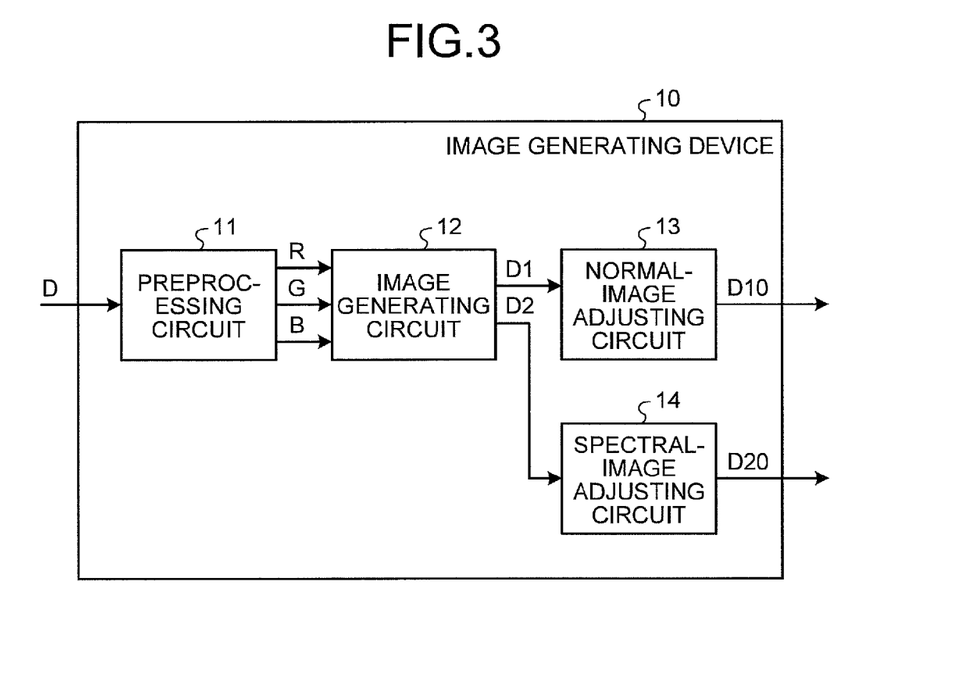
FIG. 3 is a block diagram illustrating a configuration of an image generating device according to the embodiment of the present invention.

Next, with reference to FIG. 3, an image generating device 10 mounted in the receiving device 3 is described below. The image generating device 10 includes: a preprocessing circuit 11 that performs preprocessing on data D of a baseband signal converted from a wirelessly-transmitted wireless signal and outputs each RGB color data; an image generating circuit 12 that generates a normal image D1 and a spectral image D2 from each RGB color data; a normal-image adjusting circuit 13 that performs postprocessing such as predetermined image adjustment on the normal image D1 and outputs a final normal image D10; and a spectral-image adjusting circuit 14 that performs postprocessing such as predetermined image adjustment on the spectral image D2 and outputs a final spectral image D20. More specifically, the image generating circuit 12 detects a yellow component from input each RGB color data, and generates a spectral image based on data, which is obtained by eliminating yellow-component data from G data, and B data.

Figure 4:
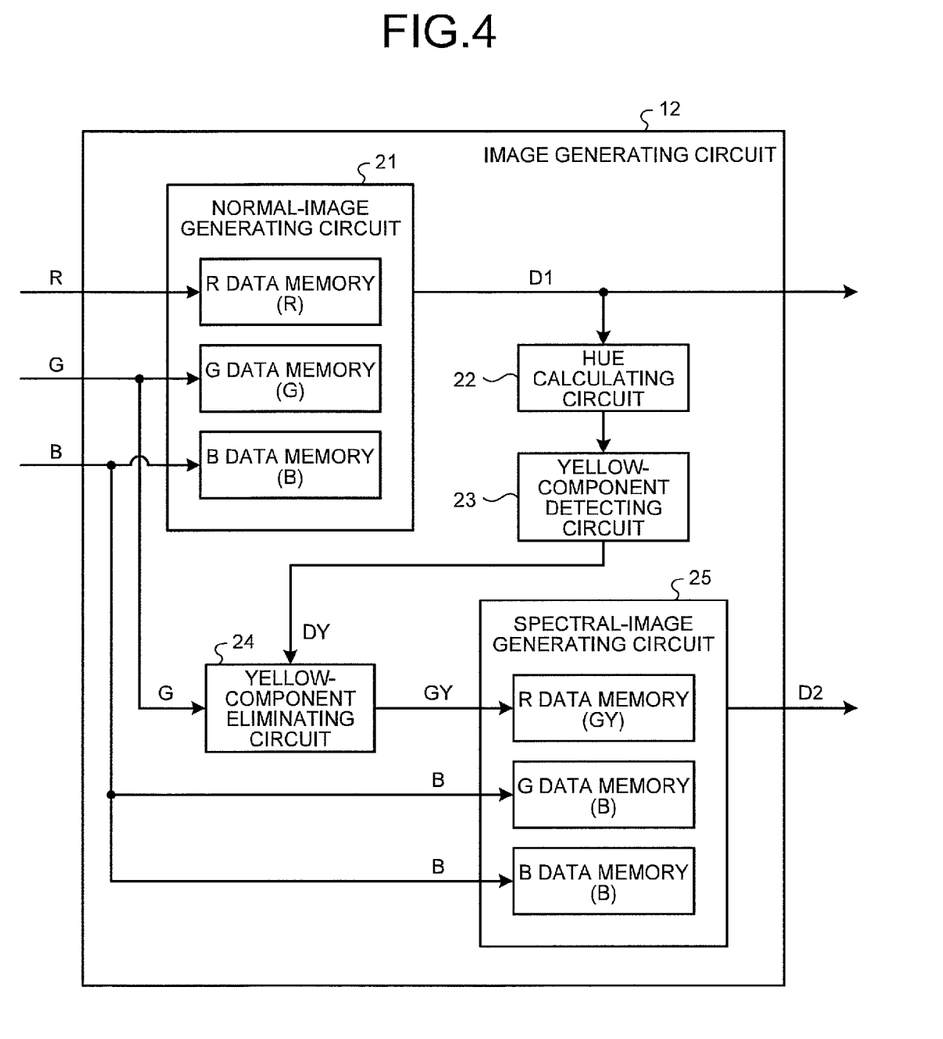
FIG. 4 is a detailed block diagram illustrating a configuration of an image generating circuit according to the embodiment of the present invention.

FIG. 4 is a block diagram illustrating a detailed configuration of the image generating circuit 12. The image generating circuit 12 includes: a normal-image generating circuit 21; a hue calculating circuit 22; a yellow-component detecting circuit 23; a yellow-component eliminating circuit 24; and a spectral-image generating circuit 25. The normal-image generating circuit 21 temporarily stores input each RGB color data in an R data memory, a G data memory, and a B data memory, combines these pieces of data as one-frame normal image data D1, and outputs the normal image data D1.

The hue calculating circuit 22 calculates hue from the normal image data D1 output from the normal-image generating circuit 21. The yellow-component detecting circuit 23 detects yellow-component data DY based on the hue calculated by the hue calculating circuit 22. The yellow-component eliminating circuit 24 generates yellow-eliminated G data GY by eliminating the yellow-component data DY from the G data input to the normal-image generating circuit 21.

The spectral-image generating circuit 25 generates and outputs spectral image data D2 from the yellow-eliminated G data, which is output from the yellow-component eliminating circuit 24, and the B data, which is input to the normal-image generating circuit 21, using contrast information for green and blue. The spectral-image generating circuit 25 temporarily stores the yellow-eliminated G data in the R data memory, temporarily stores the B data in the G data memory and the B data memory, and outputs the spectral image data D2 using the contrast information in accordance with each RGB data.

With reference to FIGS. 5A to 5D, and 6, the spectral image is described below. As represented by spectral characteristics L1 of FIG. 5A, the spectral characteristics level of the inner wall of a body cavity is high at yellow (580 nm) or red (680 nm) and thereabove. In contrast, as represented by the absorption characteristics L2 of FIG. 5B, the light absorption characteristics level of blood is maintained low other than at peaks of 415 nm (blue) and 540 nm (green). In other words, an image of the inner wall of the body cavity is generally reddish, and contrast information for color and brightness due to the spectral characteristics of the inner wall of the body cavity mostly appears in G pixels (G data) and R pixels (R data). Furthermore, contrast information for brightness due to the light absorption characteristics of blood mostly appears in B pixels (B data) and G pixels (G data).

Figure 5A:
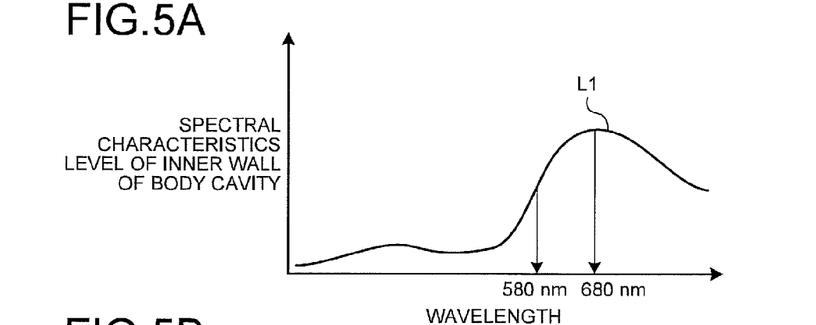
FIG. 5A is a diagram illustrating wavelength dependence of spectral characteristics of an inner wall of a body cavity according to the embodiment of the present invention.
Figure 5B:
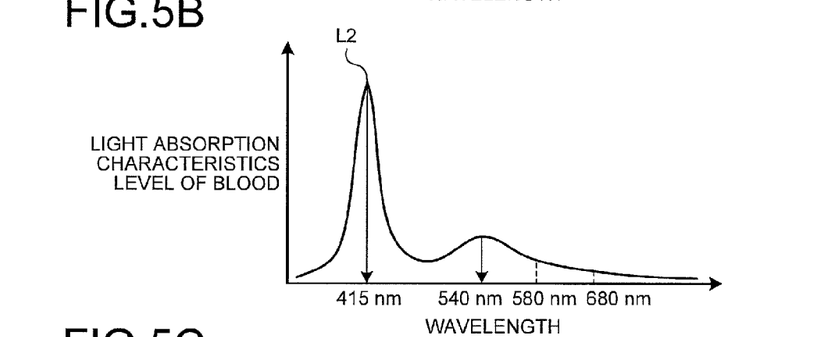
FIG. 5B is a diagram illustrating wavelength dependence of light absorption characteristics of blood according to the embodiment of the present invention.
Figure 5C:
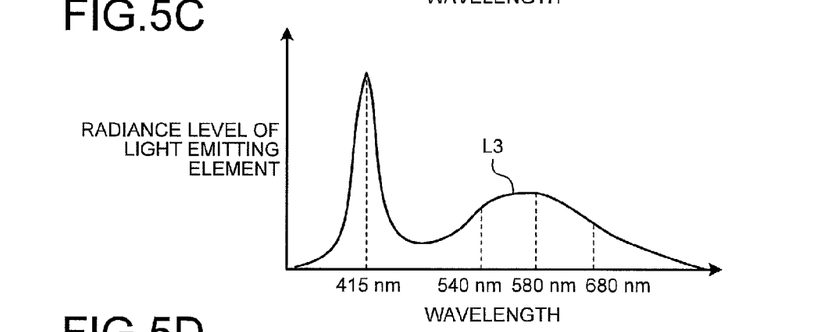
FIG. 5C is a diagram illustrating wavelength dependence of radiance of a light emitting element according to the embodiment of the present invention.
Figure 5D:
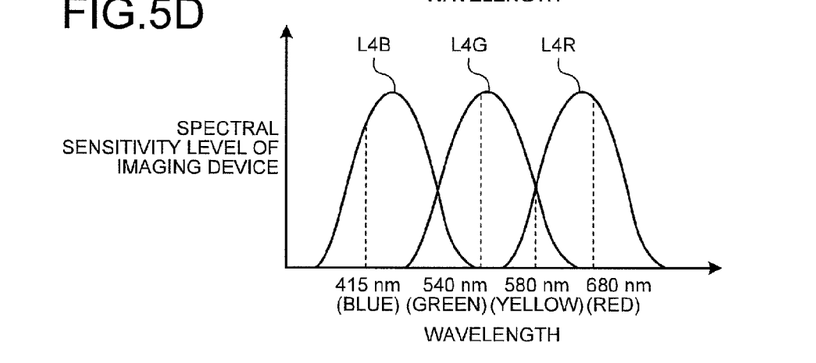
FIG. 5D is a diagram illustrating wavelength dependence of spectral characteristics of an imaging device according to the embodiment of the present invention.

Regarding the radiance level of a light emitting element, as represented by the light emission characteristics L3 of FIG. 5C, its peak wavelength appears at 415 nm similarly to the peak wavelength of the light absorption characteristics of blood, but it is not disproportionately distributed to blue (B), green (G), or red (R) as a whole, so that white light is obtained. As illustrated in FIG. 5D, regarding the spectral sensitivity level of the imaging device, B, G, R pixels respectively have spectral characteristics L4B, L4G, and L4R having peaks and distributed with centers at around 415 nm (blue), 540 nm (green), and 680 nm (red). In this case, each of the spectral characteristics L4B, L4G, and L4R has a region where some of them overlap each other. For example, the spectral characteristics L4G and L4R overlap each other at 580 nm (yellow). In other words, both G data and R data contain a yellow component.

Figure 6:
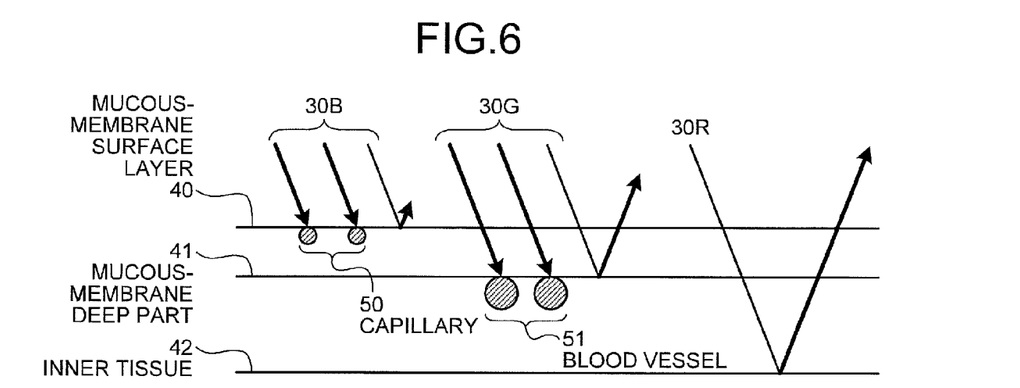
FIG. 6 is a schematic diagram illustrating a relationship between light incidence and light reflection with respect to the inner wall of the body cavity and a blood vessel.

Meanwhile, as illustrated in FIG. 6, the inner wall of the body cavity contains capillary 50 in a mucous-membrane surface layer 40, and also contains a thick blood vessel 51 in a mucous-membrane deep part 41. The light of 415 nm (blue) applied to the inner wall of the body cavity does not reach the inside of a tissue because its wavelength is short, and is absorbed by the capillary 50 due to the light absorption characteristics of blood as described above (see 30B of FIG. 6). The light of 540 nm (green) reaches the mucous-membrane deep part 41 because its wavelength is longer than blue, and is absorbed by the thick blood vessel 51 due to the light absorption characteristics of blood as described above (see 30G of FIG. 6). On the other hand, red light reaches inner tissue 42 and most of the red light is reflected as scattered light (see 30R of FIG. 6). Therefore, with application of photosensitivity to only 415 nm (blue) and 540 nm (green), it is possible to obtain contrast information of a blood vessel image of the capillary 50, the thick blood vessel 51, and the like.

Thus, a blood vessel image is obtained as the spectral image described above using the contrast information of a blood vessel and by using only B data and G data. However, because of the spectral characteristics of the spectral sensitivity of the imaging device as illustrated in FIG. 5D, a yellow component is contained in the G data, so that the resolution of the spectral image may be decreased.

To cope with this, the image generating circuit 12 described above calculates hue from each RGB data, detects a yellow component from the hue, and eliminates the yellow component from the G data, so that the contrast information for only green (540 nm) can be obtained. In contrast, contrast information for only blue (415 nm) can be obtained from the B data. The B data is allowed to contain a small amount of short-wavelength components of the G data, and the G data is allowed to contain a small amount of long-wavelength components of the B data. In other words, it is sufficient that the spectral image is generated using only the contrast information for components of 415 nm (blue) and 540 nm (green).

In the embodiment described above, the yellow component is eliminated from the G data. However, it is possible to eliminate a long-wavelength component longer than the yellow component and containing a red component. By eliminating the long-wavelength component longer than the yellow component from the G data, the G data becomes narrowband data corresponding to only a green region, so that a sharp spectral image can be obtained.

Furthermore, in the embodiment described above, the image generating device 10 is mounted in the receiving device 3. However, the present invention is not limited to this example. For example, the image generating device 10 can be mounted in the image display device 4. In this case, the receiving device 3 generates only the normal image, the recording medium 5 records only the normal image, and the image generating device 10 in the image display device 4 generates the spectral image based on RGB data forming the normal image. Spectral image may be generated as needed from a desired normal image in accordance with a generation instruction.

Figure 7:
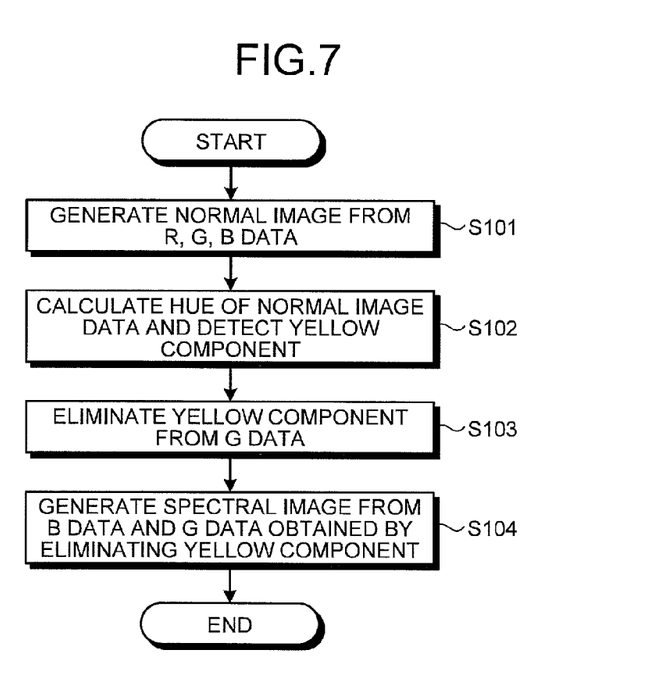
FIG. 7 is a flowchart illustrating a procedure of an image generating process according to the embodiment of the present invention.

Moreover, in the embodiment described above, the image generating device 10 is described as a circuit structure. However, it is possible to generate the normal image and the spectral image through image processing by software. That is, as illustrated in FIG. 7, the normal image is generated based on the RGB data forming the normal image (Step S101). Subsequently, hue is calculated from the data of the normal image, and a yellow component is detected from the hue (Step S102). Then, the yellow component is eliminated from the G data (Step S103). Finally, the spectral image is generated based on the B data and the G data obtained after elimination of the yellow component (Step S104), and process ends. In this case, it is possible to omit the process at Step S101 and obtain either the normal image or the spectral image through the processes at Steps S102 to S104.

According to the embodiment, it is possible to obtain a white-light normal image from acquired each RGB data, and at the same time, it is possible to obtain a spectral image of a blood vessel image and the like in which a positional relation of an object is identical to that of the normal image. Therefore, because the positional relation of an object is identical between the normal image and the spectral image, it is possible to easily and highly accurately specify a target of interest during diagnosis and the like.

In the embodiment described above, the imaging device with a Bayer array as illustrated in FIG. 2 is used. However, the present invention is not limited to this example. For example, it is possible to replace one of two G pixels in an array of R, G, G, B with a magenta (Mg) pixel so as to increase the resolution of R data and B data. By using the Mg pixel, the sensitivity of an R component and a B component can be increased, so that the resolution of the R data and the B data can be increased.

As described above, the image generating device, the endoscope system, and the image generating method according to the present invention are useful for acquiring a normal image, which is a color image of an object illuminated with white light, and a spectral image generated using a specific color component. In particular, the present invention is suitably applied to an image generating device, an endoscope system, and an image generating method capable of simultaneously obtaining a normal image and a spectral image, between which a positional relation of an identical object is identical, with a simple structure.

According to the embodiment, a first image-information generating unit generates first image information being a normal image, such as a white light image, based on a plurality of pieces of acquired color element information; a color-component detecting unit detects a predetermined color component based on each piece of color element information; a color-component eliminating unit eliminates the predetermined color component detected by the color-component detecting unit from a predetermined piece of color element information among the plurality of pieces of color element information; and a second image-information generating unit generates second color information being a spectral image, such as a blood vessel image, based on a piece of color element information obtained by eliminating the predetermined color component by the color-component eliminating unit and other pieces of color element information. Therefore, it is possible to simultaneously obtain the first image information, such as the normal image, and the second image information, such as the spectral image, between which a positional relation of an identical object is identical, with a simple structure.

The above and other features, advantages and technical and industrial significance of this invention will be better understood by reading the following detailed description of presently preferred embodiments of the invention, when considered in connection with the accompanying drawings.

What is claimed is:

1. An image generating device comprising:
   a first image-information generating unit that generates first image information based on a plurality of pieces of acquired color element information;
   a color-component detecting unit that detects a predetermined color component based on each piece of color element information;
   a color-component eliminating unit that eliminates the predetermined color component detected by the color-component detecting unit from a predetermined piece of color element information among the plurality of pieces of color element information; and a second image-information generating unit that generates second color information based on a piece of color element information obtained by eliminating the predetermined color component by the color-component eliminating unit and another piece of color element information, wherein the plurality of pieces of color element information comprises red data, green data, and blue data, the color-component detecting unit detects a yellow color component, the color-component eliminating unit generates yellow-eliminated green data by eliminating the yellow component from the green data, and the second image-information generating unit generates the second image information based on the yellow-eliminated green data and the blue data.

2. The image generating device according to claim 1, wherein the color-component detecting unit detects a long-wavelength component containing a yellow component or a red component longer than the yellow component, and the color-component eliminating unit generates color data by eliminating the long wavelength component having the yellow component or the red component longer than the yellow component from the green data.

3. The image generating device according to claim 1, wherein the second image-information generating unit generates the second image information by associating red data of the first image information with the yellow-eliminated green data, and associating each of green data and blue data of the first image information with the blue data.

4. The image generating devices according to claim 1, wherein the second image-information generating unit generates the second image information based on each piece of contrast information for the yellow-eliminated green data and the blue data.

5. An endoscope system comprising:

a first image-information generating unit that generates first image information based on a plurality of pieces of acquired color element information;

a color-component detecting unit that detects a predetermined color component based on each piece of color element information;

a color-component eliminating unit that eliminates the predetermined color component detected by the color-component detecting unit from a predetermined piece of color element information among the plurality of pieces of color element information; and a second image-information generating unit that generates second color information based on a piece of color element information obtained by eliminating the predetermined color component by the color-component eliminating unit and another piece of color element information, wherein the plurality of pieces of color element information comprises red data, green data, and blue data, the color-component detecting unit detects a yellow color component, the color-component eliminating unit generates yellow-eliminated green data by eliminating the yellow component from the green data, and the second image-information generating unit generates the second image information based on the yellow-eliminated green data and the blue data.

6. The endoscope system according to claim 5, further comprising:

an endoscope device that captures an in-vivo image of a subject; and a display device that displays the first image information and the second image information generated by the image generating device.

7. The endoscope system according to claim 6, wherein the endoscope device is a capsule endoscope.

8. An image generating method comprising:

generating first image information based on acquired red data, green data, and blue data;

calculating hue of the first image information;

detecting a yellow component based on the hue calculated at the calculating;

eliminating the yellow component from the green data; and generating second image information based on yellow-eliminated green data obtained by eliminating the yellow component from the green data at the eliminating and the blue data, wherein the yellow component is detected at the detecting, the yellow-eliminated green data is generated at the eliminating by eliminating the yellow color component from the green data, and the second image information is generated at the generating the second image information based on the yellow-eliminated green data and the blue data.

9. An image generating device comprising:

a first image-information generating means that generates first image information based on a plurality of pieces of acquired color element information;

a color-component detecting means that detects a predetermined color component based on each piece of color element information;

a color-component eliminating means that eliminates the predetermined color component detected by the color-component detecting means from a predetermined piece of color element information among the plurality of pieces of color element information; and a second image-information generating means that generates second color information based on a piece of color element information obtained by eliminating the predetermined color component by the color-component eliminating means and another piece of color element information, wherein the plurality of pieces of color element information comprises red data, green data, and blue data, the color-component detecting means detects a yellow color component, the color-component eliminating means generates yellow-eliminated green data by eliminating the yellow component from the green data, and the second image-information generating means generates the second image information based on the yellow-eliminated green data and the blue data.

* * * * *